(12) United States Patent
Da Cruz

(10) Patent No.: US 7,661,955 B2
(45) Date of Patent: Feb. 16, 2010

(54) DENTAL APPLIANCE

(76) Inventor: Joseph Da Cruz, 6/2 Rutledge Plaza, Queanbeyan, New South Wales (AU) 2620

( * ) Notice: Subject to any disclaimer, the term of this patent is extended or adjusted under 35 U.S.C. 154(b) by 146 days.

(21) Appl. No.: 10/573,986

(22) PCT Filed: Sep. 22, 2004

(86) PCT No.: PCT/AU2004/001296

§ 371 (c)(1),
(2), (4) Date: Sep. 6, 2006

(87) PCT Pub. No.: WO2005/032396

PCT Pub. Date: Apr. 14, 2005

(65) Prior Publication Data
US 2007/0059659 A1    Mar. 15, 2007

(30) Foreign Application Priority Data
Oct. 3, 2003    (AU) ............................... 2003905455

(51) Int. Cl.
*A61C 3/00*    (2006.01)
(52) U.S. Cl. .................. 433/7; 433/6; 433/18; 433/20; 433/24
(58) Field of Classification Search .................. 433/6, 433/7, 18, 20–22, 24
See application file for complete search history.

(56) References Cited

U.S. PATENT DOCUMENTS

| | | | |
|---|---|---|---|
| 3,967,379 A | | 7/1976 | Bergersen |
| 3,977,082 A | * | 8/1976 | Siatkowski ..................... 433/7 |
| 3,994,068 A | * | 11/1976 | Goshgarian ..................... 433/6 |
| 4,026,023 A | * | 5/1977 | Fisher ........................... 433/7 |
| 4,224,021 A | * | 9/1980 | Foxman .......................... 433/2 |
| 4,253,828 A | | 3/1981 | Coles et al. |
| 4,299,568 A | * | 11/1981 | Crowley ......................... 433/6 |
| 4,413,978 A | * | 11/1983 | Kurz .............................. 433/6 |
| 4,431,411 A | * | 2/1984 | Witzig et al. ................... 433/6 |
| 5,002,485 A | * | 3/1991 | Aagesen ......................... 433/7 |
| 5,064,370 A | * | 11/1991 | Jones ........................... 433/21 |
| 5,096,416 A | * | 3/1992 | Hulsink ......................... 433/6 |
| 5,376,001 A | | 12/1994 | Tepper |

(Continued)

FOREIGN PATENT DOCUMENTS

JP    2002/191623 A    7/2002

*Primary Examiner*—Cris L Rodriguez
*Assistant Examiner*—Hao D Mai
(74) *Attorney, Agent, or Firm*—Kenyon & Kenyon LLP

(57) ABSTRACT

A removable dental appliance having a base adapted for locating inside of an arch of teeth of a wearer and an arch wire coupled to the base, wherein an outer surface of the base is contoured for contact with inner surfaces of the teeth, and wherein when in use the arch wire extends around an outer periphery of a set of the wearer's teeth such that no interconnection between the arch wire and the base exists intermediate the set of teeth. A removable dental appliance having a base adapted for locating inside of an arch of teeth of a wearer and an arch wire coupled to the base, wherein an outer surface of the base is contoured for contact with inner surfaces of a set of teeth on one side of the wearer's jaw, and wherein when in use the arch wire extends around an outer periphery of the set of teeth such that no interconnection between the arch wire and the base exists intermediate the set of teeth.

11 Claims, 19 Drawing Sheets

U.S. PATENT DOCUMENTS

| | | | |
|---|---|---|---|
| 5,607,300 A * | 3/1997 | Tepper | 433/6 |
| 5,785,520 A * | 7/1998 | Carano et al. | 433/7 |
| 6,332,774 B1 * | 12/2001 | Chikami | 433/20 |
| 6,908,306 B2 * | 6/2005 | Bowman et al. | 433/18 |
| 2003/0013062 A1 * | 1/2003 | White | 433/21 |
| 2005/0037312 A1 * | 2/2005 | Uchida | 433/6 |
| 2005/0186524 A1 * | 8/2005 | Abolfathi et al. | 433/7 |
| 2006/0099546 A1 * | 5/2006 | Bergersen | 433/6 |

* cited by examiner

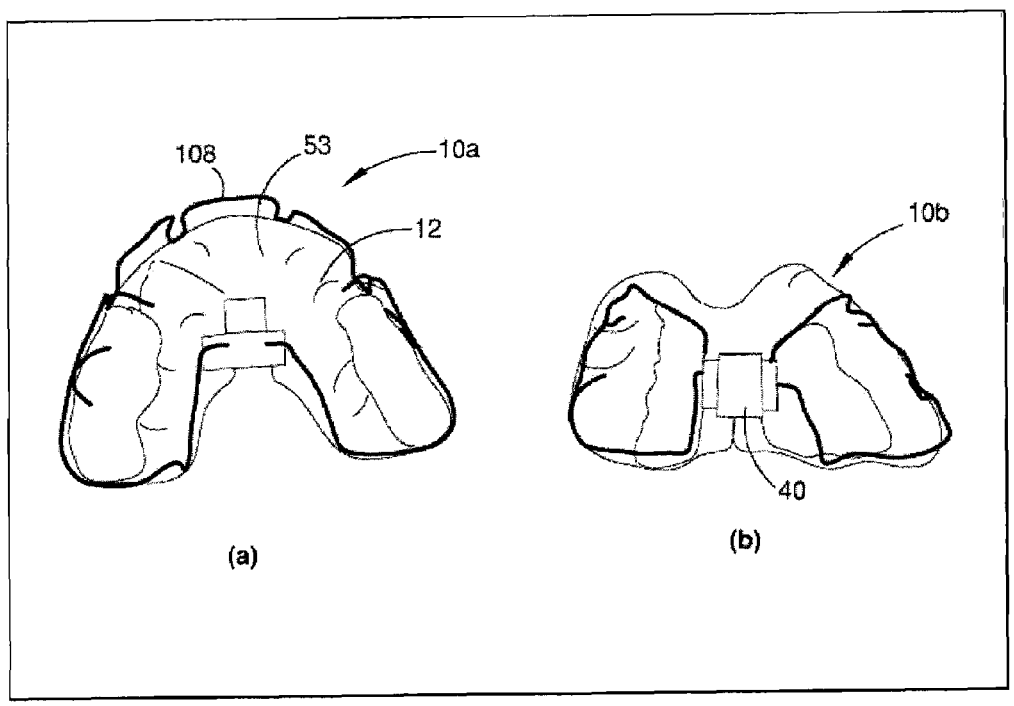
Figure 13a + 13b

DENTAL APPLIANCE

This is a 371 national phase application of PCT/AU2004/001296 filed 22 Sep. 2004, claiming priority to Australian Application No. 2003905455 filed 3 Oct. 2003, the contents of which are incorporated herein by reference.

FIELD OF THE INVENTION

This invention relates to a dental appliance, and more particularly, but not exclusively, to a removable dental appliance for use in orthodontic correction, temporomandibular joint ("TMJ") splint therapy and/or myofunctional activities to alter muscle function and facial and dental development. Examples of the invention relate to influencing movement of cranium bones and sutural movement, and to creating/improving muscle relaxation and breathing through the nose.

BACKGROUND OF THE INVENTION

Conventional removable dental appliances are located and retained on a wearer's jaw by use of clasps which fit firmly around a selected number of teeth. One form of clasp is known as an Adams' clasp, and, in general, fits tightly around a single tooth. It is usual for a conventional removable dental appliance to be anchored to the wearer's jaw by several such clasps so that the appliance is held firmly in place. However, such tight fitting of the dental appliance to the wearer's jaw often leads to the appliance being difficult to install, particularly if the wearer's teeth are tilted. Moreover, such conventional removable dental appliances often fit very tightly to the wearer's jaw, affecting movement of the wearer's skull bones causing discomfort and stress, both mentally and also physically (for example in the clenching of the wearer's face). The clasps used to hold the appliance in place by being anchored to particular teeth provide little or no freedom for the teeth to move. As such, the teeth are not able to make room for other teeth, and tooth extractions are commonly necessary.

The discomfort experienced by patients in wearing conventional removable dental appliances often makes the patient unwilling to wear the appliance, thus leading to a low level of compliance which has an adverse affect on the treatment which typically requires the appliance to be worn often and for extended periods. Further, if a patient does not wear the appliance for even just a few days, the teeth may move such that the appliance no longer fits properly. In such situations, it may be necessary for a new impression of the patient's jaw to be taken and for the appliance to be modified or replaced, which can be expensive and counter-productive in terms of achieving the desired effect for which the appliance is being used. Clasps such as Adams' clasps are also prone to breakage, particularly in situations where the appliance is difficult to install, and are also commonly incompatible for use with child patients who may not have sufficiently erupted teeth for the clasps to locate properly.

Examples of the present invention seek to overcome or at least alleviate the above disadvantages of conventional removable dental appliances.

SUMMARY OF THE INVENTION

In accordance with one aspect of the present invention, there is provided a removable dental appliance having a base adapted for locating inside of an arch of teeth of a wearer and an arch wire coupled to the base, wherein an outer surface of the base is contoured for contact with inner surfaces of the teeth, when in use the arch wire extends around an outer periphery of a set of the wearer's teeth such that no interconnection between the arch wire and the base exists intermediate the set of teeth, and the dental appliance is provided with one or more expansion screws for expanding the base.

In accordance with another aspect of the present invention, there is provided a removable dental appliance having a base adapted for locating inside of an arch of teeth of a wearer and an arch wire coupled to the base, wherein an outer surface of the base is contoured for contact with inner surfaces of the teeth, and wherein when in use the arch wire extends around an outer periphery of a set of the wearer's teeth such that no interconnection between the arch wire and the base exists intermediate the set of teeth.

Preferably, the arch wire extends from one side posterior portion of the base to the other side posterior portion of the base for contact with outer surfaces of the set of teeth along an outside of the arch.

Preferably, the arch wire extends rearwardly relative to the posterior portions on each side of the base so as to allow limited movement of the arch wire relative to the base when the dental appliance is in use.

Preferably, the dental appliance is for an upper jaw of the wearer.

Preferably, when the dental appliance is in use, the arch wire extends continuously from a left side posterior portion of the base, outwardly behind a posterior tooth on the left side of the arch, forwardly along the outside left side of the arch, rightward along the outside front side of the arch, rearwardly along the outside right side of the arch, and inwardly behind a posterior tooth on the right side of the arch to a right side posterior portion of the base.

Preferably, the arch wire incorporates a plurality of U-loops. In one example, the arch wire incorporates four U-loops.

Preferably, the arch wire is provided with one or more C-clasps. More preferably, at least one of the C-clasps is coupled to the arch wire at only one end portion of the C-clasp.

Preferably, the arch wire is provided with one or more L-rests.

Preferably, the base is acrylic. Preferably, the base is provided with a bite plane. In one example the bite plane is an anterior bite plane. In an alternative example the bite plane is a posterior bite plane.

In accordance with another aspect of the present invention, there is provided a removable dental appliance having a base adapted for locating inside of an arch of teeth of a wearer and an arch wire coupled to the base, wherein an outer surface of the base is contoured for contact with inner surfaces of a set of teeth on one side of the wearer's jaw, when in use the arch wire extends around an outer periphery of the set of teeth such that no interconnection between the arch wire and the base exists intermediate the set of teeth, and the dental appliance has anterior wires or springs for urging forward anterior teeth of the wearer.

In accordance with another aspect of the invention, there is provided a removable dental appliance having a base adapted for locating inside of an arch of teeth of a wearer and an arch wire coupled to the base, wherein an outer surface of the base is contoured for contact with inner surfaces of a set of teeth on one side of the wearer's jaw, and wherein when in use the arch wire extends around an outer periphery of the set of teeth such that no interconnection between the arch wire and the base exists intermediate the set of teeth.

Preferably, the arch wire extends continuously from a posterior portion of the base, outwardly behind a posterior tooth of said set of teeth, forwardly in contact with outer surfaces of said set of teeth, and inwardly in front of a front tooth of said set of teeth to the base.

Preferably, the removable dental appliance is for a lower jaw of the wearer.

Preferably, the base has a first lingual portion and an opposed second lingual portion, the first and second lingual portions being held apart by a resilient member, the first lingual portion is contoured for contact with inner surfaces of a first set of teeth on one side of the wearer's jaw and the second lingual portion is contoured for contact with inner surfaces of a second set of teeth on an opposite side of the wearer's jaw, and when in use, a first arch wire extends continuously from a posterior portion of the first lingual portion, outwardly behind a posterior tooth of said first set of teeth, forwardly in contact with outer surfaces of said first set of teeth, and inwardly in front of a front tooth of said first set of teeth to the first lingual portion, and a second arch wire extends continuously from a posterior portion of the second lingual portion, outwardly behind a posterior tooth of said second set of teeth, forwardly in contact with outer surfaces of said second set of teeth, and inwardly in front of a front tooth of said second set of teeth to the second lingual portion.

Preferably, each of the first and second arch wires is provided with one or more C-clasps. More preferably, at least one of the C-clasps is coupled to the arch wire at only one end portion of the C-clasp.

BRIEF DESCRIPTION OF THE DRAWINGS

Preferred embodiments of the invention will now be described, by way of example only, with reference to the accompanying drawings, in which:

FIG. 13(a) is a perspective view of an underside of a dental appliance for an upper jaw;

FIG. 13(b) is a perspective view of an underside of a dental appliance for an upper jaw, the appliance having no anterior bite plane;

DETAILED DESCRIPTION

Figure 1:
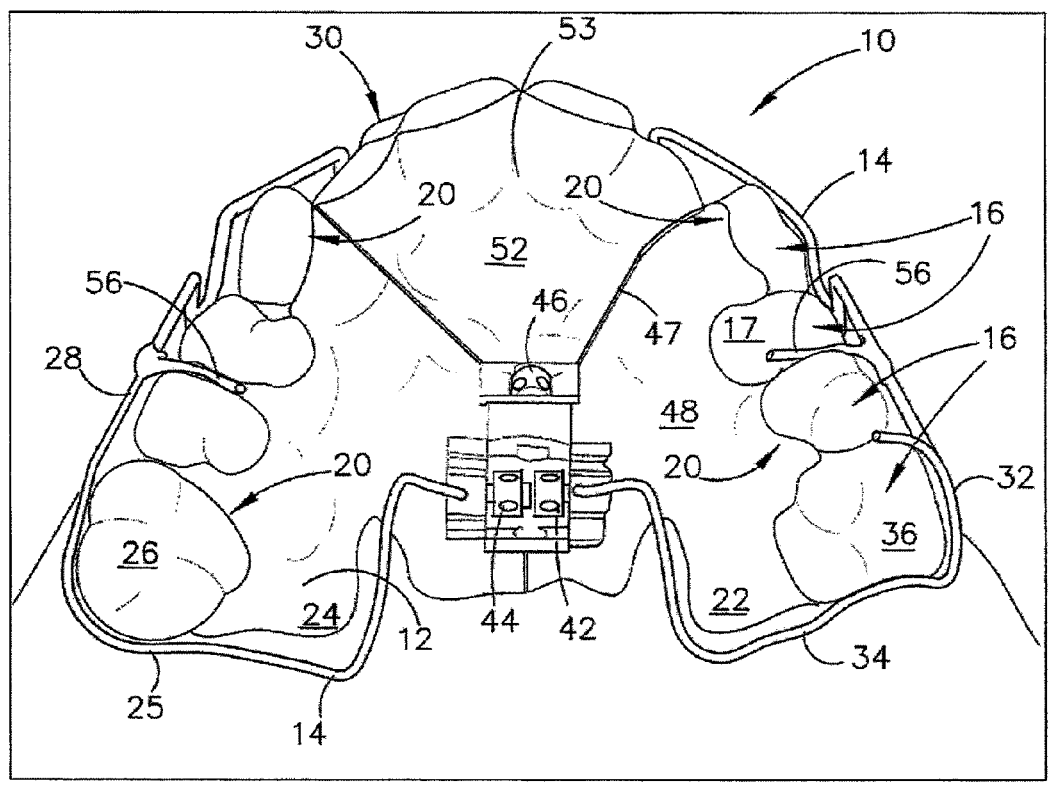
FIG. 1 is a perspective view of an underside (ie. the surface which in situ faces away from tissue of the upper jaw) of a dental appliance for an upper jaw.
Figure 2:
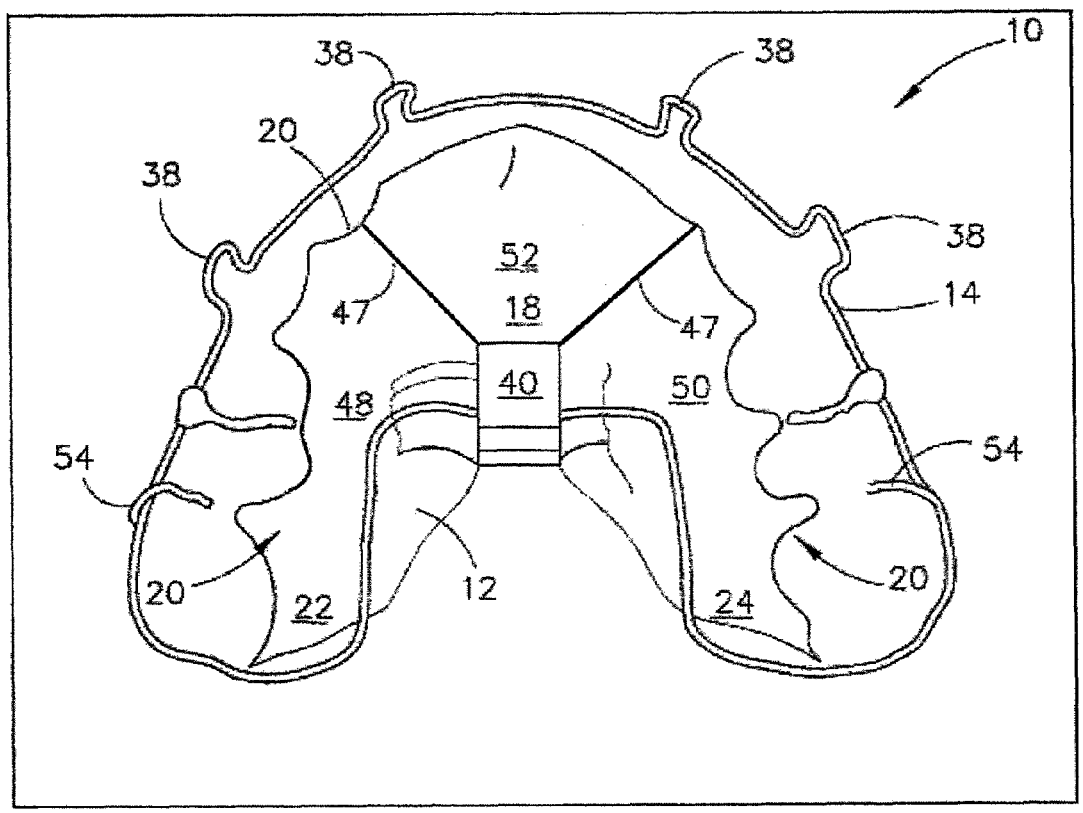
FIG. 2 is a perspective view of an upper surface (ie. the surface which in situ faces the tissue of the upper jaw) of the dental appliance shown in FIG. 1.
Figure 3:
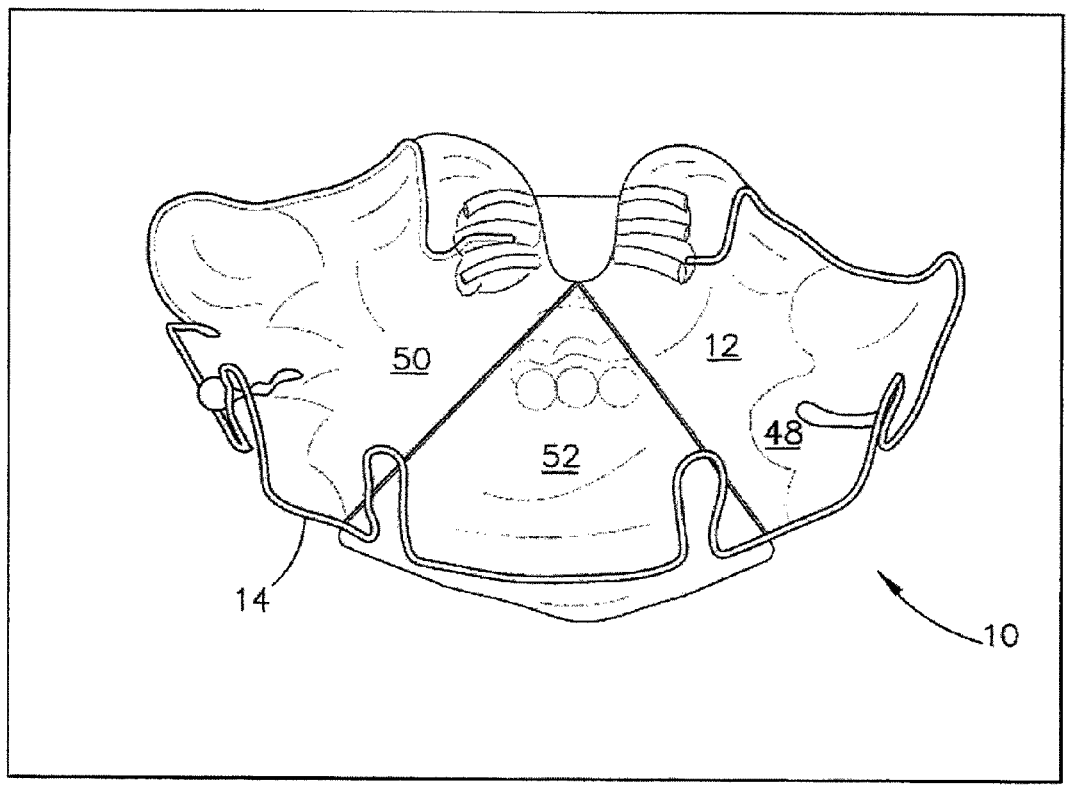
FIG. 3 is a front perspective view of the dental appliance shown in FIGS. 1 and 2.

The removable dental appliance 10 shown in FIGS. 1 to 3 is for an upper jaw of a wearer and has an acrylic base 12 with a labial arch wire 14 coupled to the base 12. FIG. 1 shows the dental appliance fitted to a model upper jaw. The base 12 of the dental appliance is shaped for being located inside of an arch 16 of teeth of the wearer in that the base 12 is formed with a curved upper portion 18 for resting against a roof of the wearer's mouth. An outer surface 20 of the base 12 is contoured for contact with inner surfaces of the wearer's teeth 17. The arch wire 14 extends from one side posterior portion 22 of the base 12 to the other side posterior portion 24 of the base 12 for contact with outer surfaces of the teeth 17 along an outside of the arch 16.

The base 12 may be formed from cold cured or heat cured denture acrylic, and may be trimmed or otherwise adjusted according to the pressure required to be applied to the teeth.

As can be seen in FIG. 1, when the dental appliance 10 is in use, the arch wire 14 extends continuously from a left side posterior portion 24 of the base 12, outwardly (see reference numeral 25) behind a posterior tooth 26 on the left side of the arch 16, forwardly (see reference numeral 28) along the outside left side of the arch 16, rightward (see reference numeral 30) along the outside front side of the arch 16, rearwardly (see reference numeral 32) along the outside right side of the arch 16, and inwardly (see reference numeral 34) behind a posterior tooth 36 on the right side of the arch 16 to a right side posterior portion 22 of the base 12. The arch wire 14 also incorporates four U-loops 38 which may be adjusted to tailor the effect provided by use of the dental appliance 10. Although in other examples more than or less than four U-loops may be formed in the arch wire 14, the applicant has determined that four U-loops provides the arch wire 14 with an appropriate degree of flexibility whilst keeping good retention properties.

As the arch wire 14 extends rearwardly relative to the posterior portions 22, 24, spacing is achieved between the arch wire 14 and the base 12 so as to allow improved freedom of movement between the arch wire 14 and the base 12 during use. This assists in preventing too tight a fit which can cause tight locking of the maxilla and undue stress to the wearer. By promoting muscle relaxation in the wearer, clenching and other muscular movements detrimental to jaw alignment are avoided or at least reduced, and breathing is enhanced through improvement of the airway.

The enhanced freedom of movement of the arch wire 14 relative to the base 12 also facilitates a "spring fit" of the appliance, where it is snapped into place in a wearer's mouth. Advantageously, additional flexibility in the fit of the appliance is achieved, and greater scope is provided for adjustment of the appliance.

The dental appliance 10 shown in FIGS. 1 to 3 is also provided with a 3-way expansion screw mechanism 40 which has three expansion screws 42, 44, 46 for enlarging the maxilla of the wearer in left, right and anterior directions. Each of the expansion screws 42, 44, 46 is provided with apertures for receiving a tool (not shown) which is used by an orthodontist or patient to adjust the effective size of the base 12 according to the shape desired in the wearer's maxilla. The base 12 is able to expand in response to adjustment of the expansion screws 42, 44, 46 by virtue of breaks 47 formed in the base 12 which divide it into three separate panels 48, 50, 52. The effect provided by the expansion screws 42, 44, 46 in this arrangement is advantageous as the arch wire 14 is around the arch 16 and there is nothing grabbing or hurting the teeth 17 as is often the case with conventional previously proposed dental appliances. As such, the present arrangement provides benefits in influencing the nervous system and muscle function of the wearer.

The base 12 has an anterior bite plane 53 which may be formed so as to be either flat or sloped in order to bring the wearer's lower jaw forward when the lower jaw is occluding the bite plane 53 and to relax the wearer's chin and neck muscles. The acrylic base 12 is formed according to the shape desired to be given to the wearer's jaw. The anterior bite plane helps to put the wearer's teeth together so that there is no deep bite and the right amount of bottom teeth are showing. Over time, a deep bite is able to be corrected and clenching is able to be reduced through the use of an anterior bite plane which operates as a clenching inhibitor. Further, the effect of the bite plane and the widening of the maxilla may help to relieve TMJ problems and may help to encourage opening of the mouth of a wearer previously suffering a jaw opening restriction. Posterior bite planes can also be used instead of anterior bite planes, for example in the case of Class III malocclusions, especially in children.

A C-clasp 54 is soldered onto each side of the arch wire 14 to assist retention of the dental appliance 10 to the wearer's teeth 17. Each side of the arch wire 14 is also provided with an L-rest 56 for preventing the arch wire 14 from dropping.

The dental appliances 10 shown in FIGS. 4, 5 and 6, 7 are similar in many respects to the dental appliance 10 shown in FIGS. 1 to 3, and like features are indicated by like reference numerals. The dental appliance shown in FIGS. 4 and 5 does differ however in that it has changed, more asymmetric, geometry to suit a specific case of patient, a 1-way expansion screw mechanism 58 (and correspondingly only one break 47 in the base 12 required for size adjustment of the base 12), and the arch wire 14 having only two U-loops 38. The dental appliance 10 shown in FIGS. 6 and 7 also has accentuated asymmetric geometry, and a 1-way expansion screw mechanism 58, but has six U-loops 38 incorporated into the arch wire 14.

Figure 4:
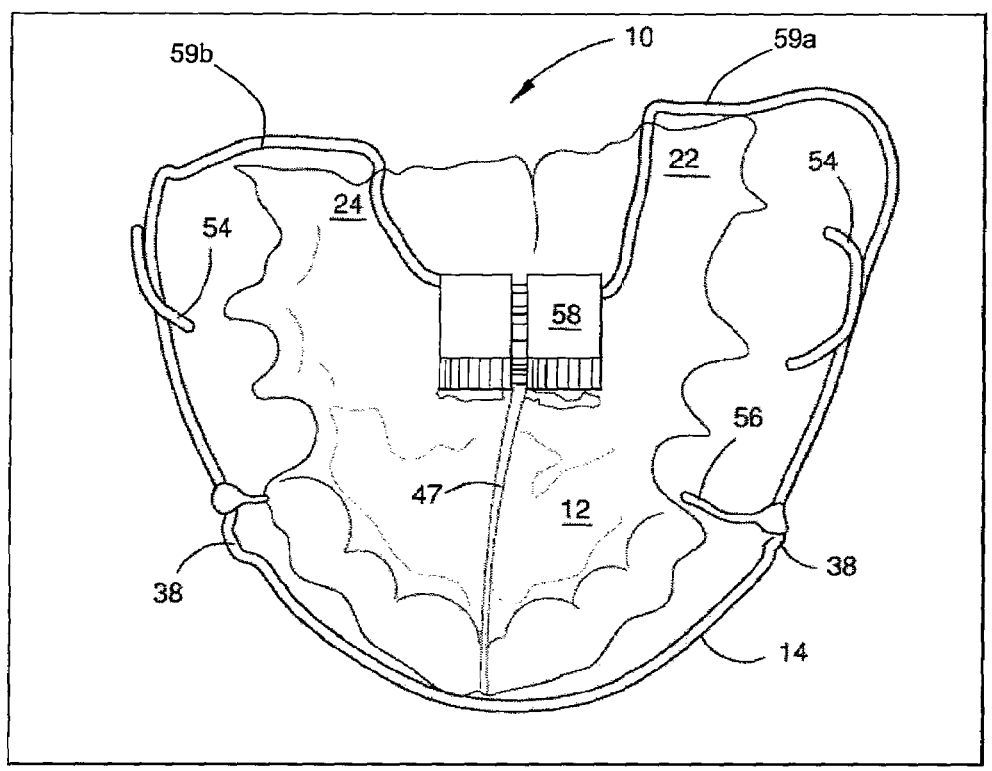
FIG. 4 is a top view of a dental appliance for an upper jaw.
Figure 5:
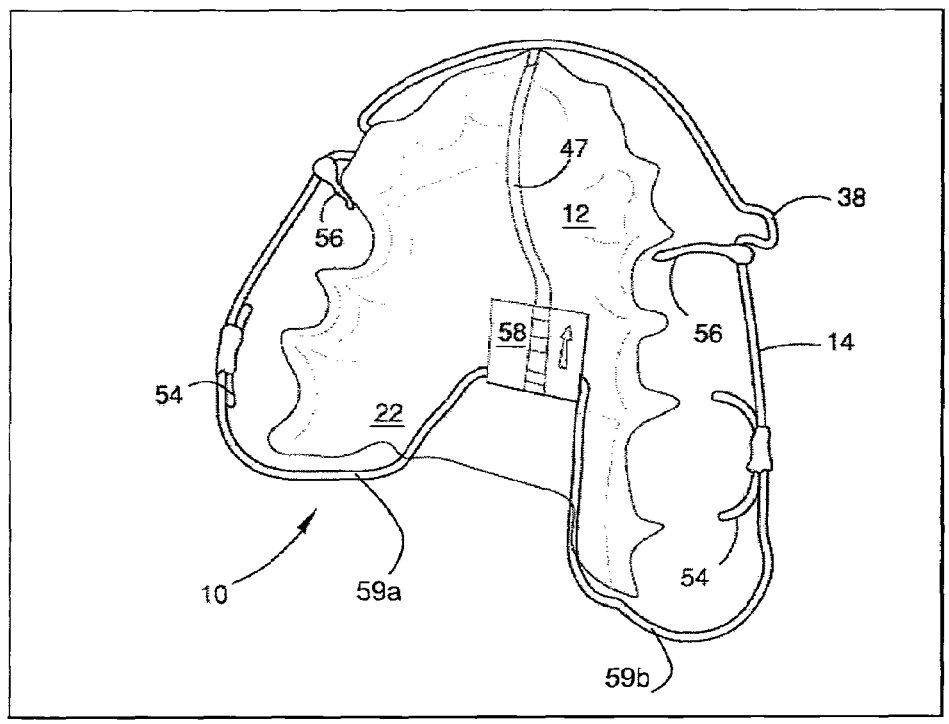
FIG. 5 is a side perspective view of an underside of the dental appliance shown in FIG. 4.
Figure 6:
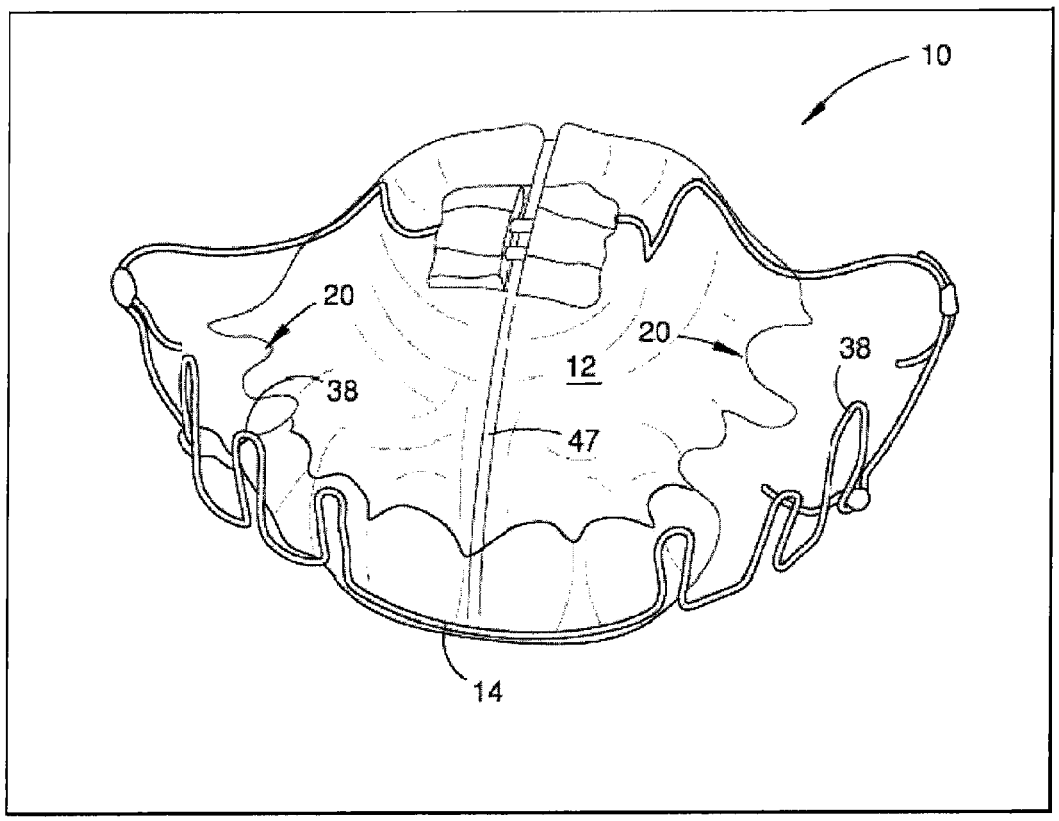
FIG. 6 is a front perspective view of an underside of a dental appliance for an upper jaw.
Figure 7:
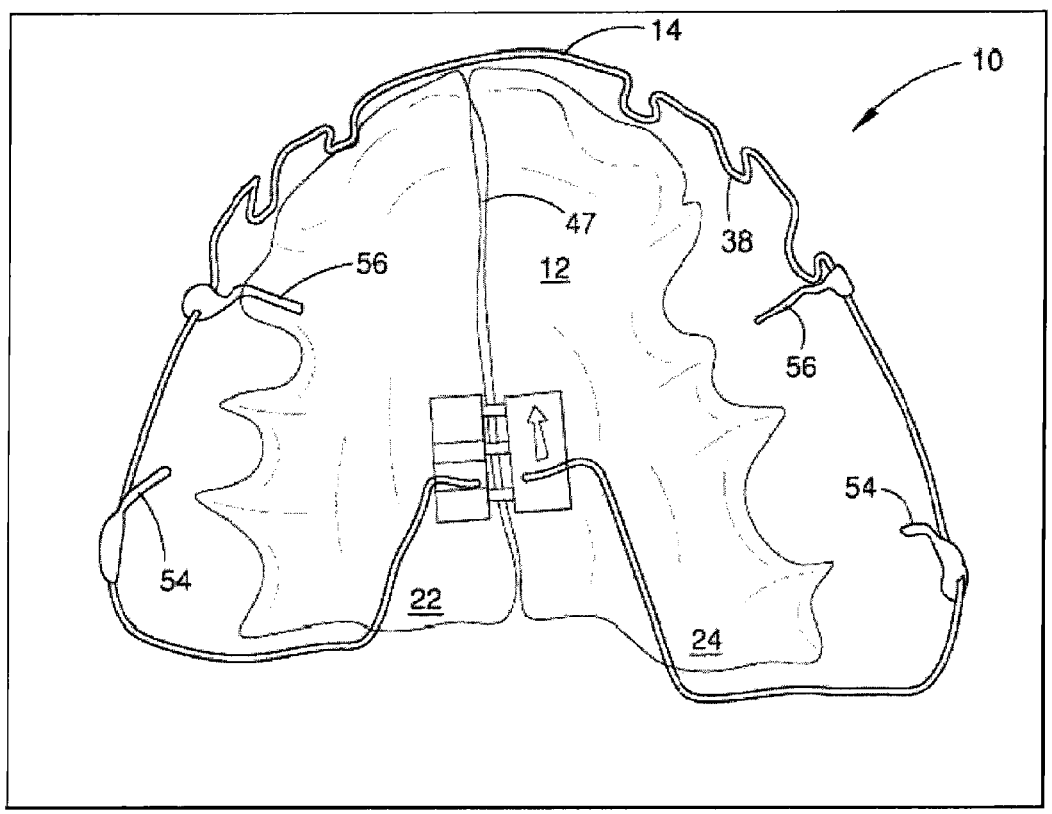
FIG. 7 is a plan view of an underside of the dental appliance shown in FIG. 6.

FIGS. 4 and 5 show that the arch wire 14 extends from one side posterior portion 22 of the base 12 to the other side posterior portion 24 of the base 12 for contact with outer surfaces of the set of teeth 17 along an outside of the arch 16 of teeth. The arch wire 14 exits the posterior portions 22, 24 on each side of the base 12 at locations spaced from the arch 16 of teeth, the arch wire 14 extending from the posterior portions 22, 24 indirectly, generally rearwardly and outwardly relative to the wearer when in situ, to the set of teeth 17 in bent portions 59a, 59b of wire on each side of the base 12 so as to allow flexure of the bent portions 59a, 59b of wire between the base 12 and the set of teeth 17, thereby promoting limited movement of the arch wire 14 relative to the base 12 when the dental appliance 10 is in use. At each side posterior portion 22, 24 the arch wire 14 extends within the base 12 to the expansion screw mechanism 58 so as to form a closed circuit.

Dental appliances made according to examples of the present invention, in particular by virtue of the arrangement of the arch wire, allow smooth fitting of the appliance while still providing adequate pressure on teeth to be moved.

Figure 8:
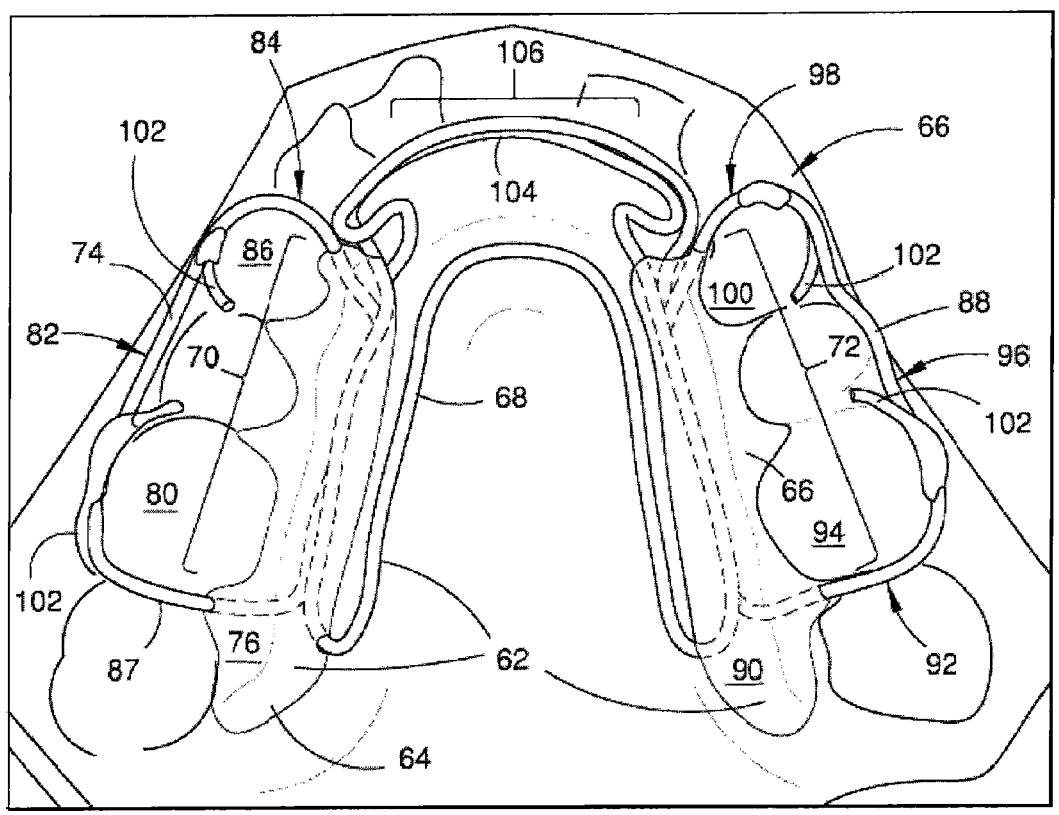
FIG. 8 is a top view of a dental appliance for a lower jaw.
Figure 9:
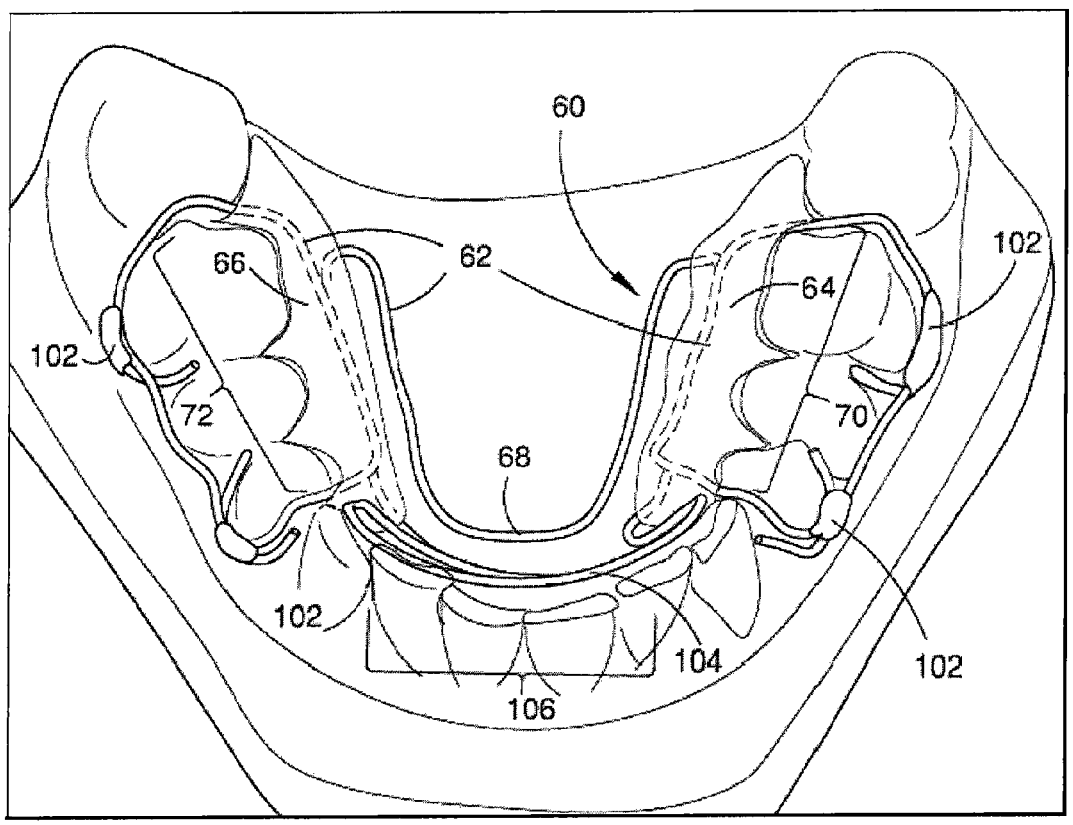
FIG. 9 is a front perspective view of the dental appliance shown in FIG. 8.
Figure 10:
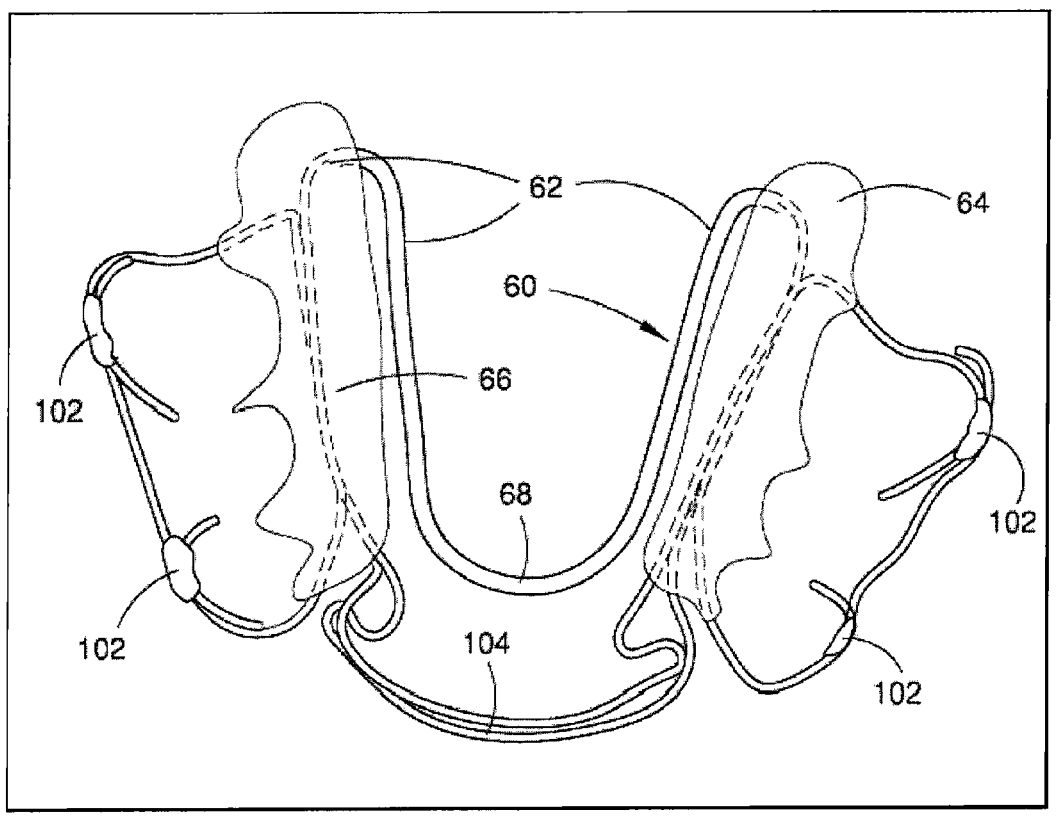
FIG. 10 is a top view of the dental appliance shown in FIGS. 8 and 9.

The removable dental appliance 60 shown in FIGS. 8, 9 and 10 is for a lower jaw of a wearer, and is shown in FIGS. 8 and 9 as being fitted to a model of a lower jaw. The dental appliance 60 has a base 62 which is formed of a first lingual portion 64, a second lingual portion 66 and a resilient member 68 in the form of a kind of W-type coffin spring. The first and second lingual portions 64,66 are held apart by the resilient member 68 which may be adjusted to widen the wearer's mandible, particularly in cases where the wearer also has fitted a dental appliance on his or her upper jaw and it is necessary to widen the mandible to keep up with a widening of the maxilla. The first lingual portion 64 is contoured for contact with inner surfaces of a first set 70 of teeth on one side of the wearer's lower jaw, and the second lingual portion 66 is contoured for contact with inner surfaces of a second set 72 of teeth on an opposite side of the wearer's lower jaw. As is shown in FIG. 8, when in use a first arch wire 74 extends continuously from a posterior portion 76 of the first lingual portion 64, outwardly (see reference numeral 78) behind a posterior tooth 80 of said first set 70 of teeth, forwardly (see reference numeral 82) in contact with outer surfaces of said first set 70 of teeth, and inwardly (see reference numeral 84) in front of a front tooth 86 of said first set 70 of teeth to the first lingual portion 64. Similarly, a second arch wire 88 extends continuously from a posterior portion 90 of the second lingual portion 66, outwardly (see reference numeral 92) behind a posterior tooth 94 of said second set 72 of teeth, forwardly (see reference numeral 96) in contact with outer surfaces of said second set 72 of teeth, and inwardly (see reference numeral 98) in front of a front tooth 100 of said second set 72 of teeth to the second lingual portion 66. Preferably, each of the first and second sets of teeth 70,72 includes teeth from premolar to molars.

Each of the first and second arch wires 74, 88 is provided with two C-clasps 102, soldered to the respective arch wire 74, 88 to assist retention of the dental appliance 60 to the wearer's lower jaw. The dental appliance 60 is also provided with anterior wires or springs 104 for urging forward anterior teeth 106 of the wearer.

The base 62 may be trimmed or otherwise adjusted according to the pressure required to be applied to the teeth.

Figure 11:
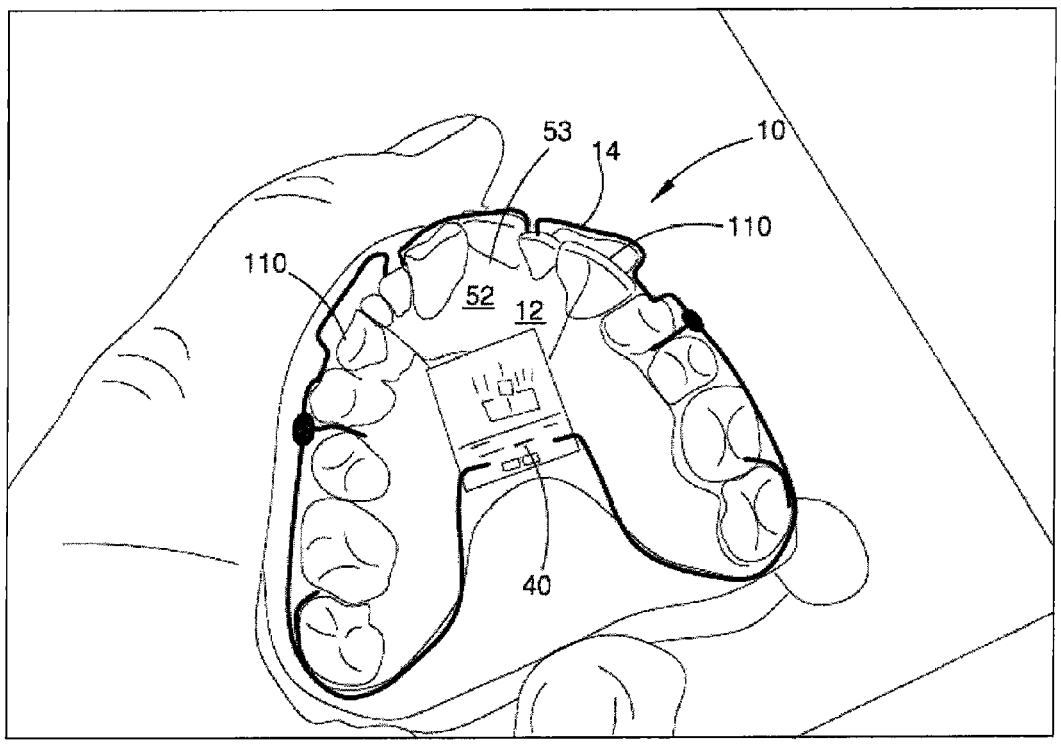
FIG. 11 is a perspective view of an underside of a dental appliance for an upper jaw.
Figure 12:
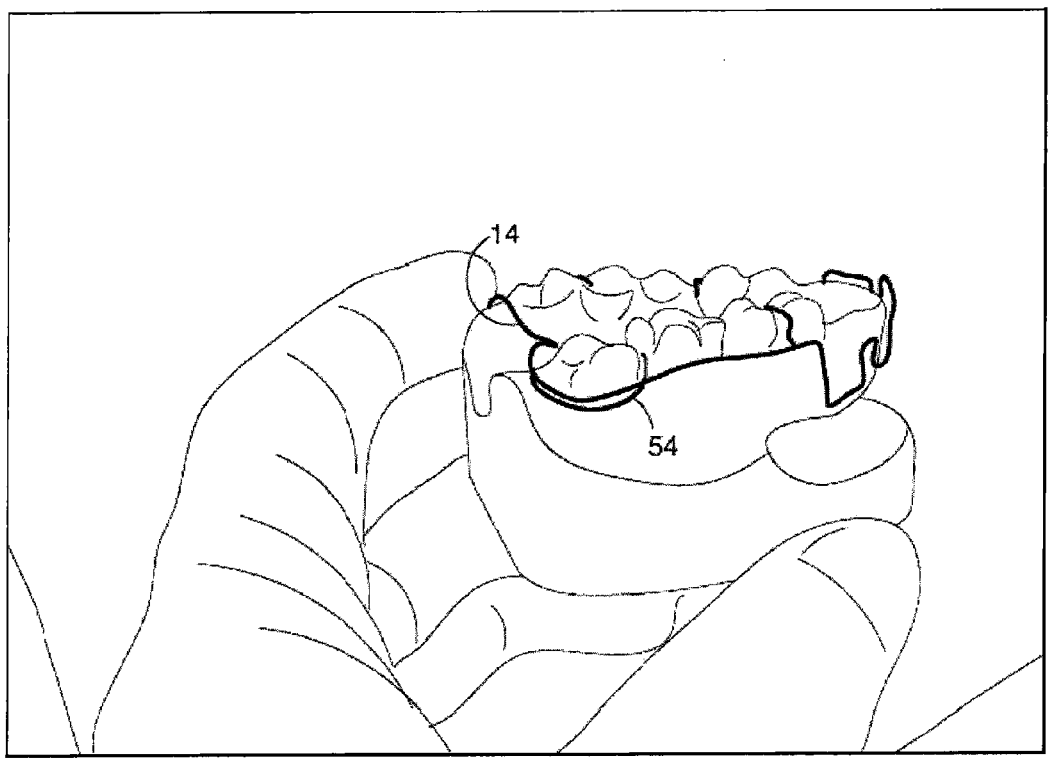
FIG. 12 is a side view of the dental appliance shown in FIG. 11.

FIGS. 11 and 12 show a removable dental appliance 10 fitted to a model upper jaw. The appliance is provided with a 3-way expansion screw mechanism 40, and has an anterior bite plane 53. An arch wire is provided with C-clasps 54. As is best seen in FIG. 12, the C-clasps in this case are attached to the arch wire 14 at only one end portion thereof, so as to provide improved retention by way of the "long" C-clasp having a longer cantilever portion when compared to a C-clasp attached at a centre portion thereof to the arch wire. The cantilever portion is thus able to flex relative to the arch wire 14 to a greater degree. As is also best seen in FIG. 4, the arch wire 14 is provided with L-rests 56 to prevent the arch wire 14 from dropping relative to the patient's teeth.

FIG. 13(a) shows a 3-way adjustable removable dental appliance 10a for an upper jaw, a base 12 of the appliance 10a having an anterior bite plane 53. The appliance 10a has a an arch wire 14 with a front labial bow portion 108 for abutment against the labial surfaces of the front teeth of the upper jaw. FIG. 13(b) shows an alternative removable dental appliance 10 for the same patient wherein there is no anterior bite plane or labial bow to the arch wire 14 such that the appliance enables the patient to speak more easily, and no wire shows across the front of the patient's upper teeth. In FIG. 13(b), as there is no front portion of the base 12 for abutment against the lingual surfaces of the front teeth of the upper jaw, no provision is made for enlarging the base 12 in the forward direction and a 2-way expansion screw mechanism 40 is sufficient.

Figure 13C:
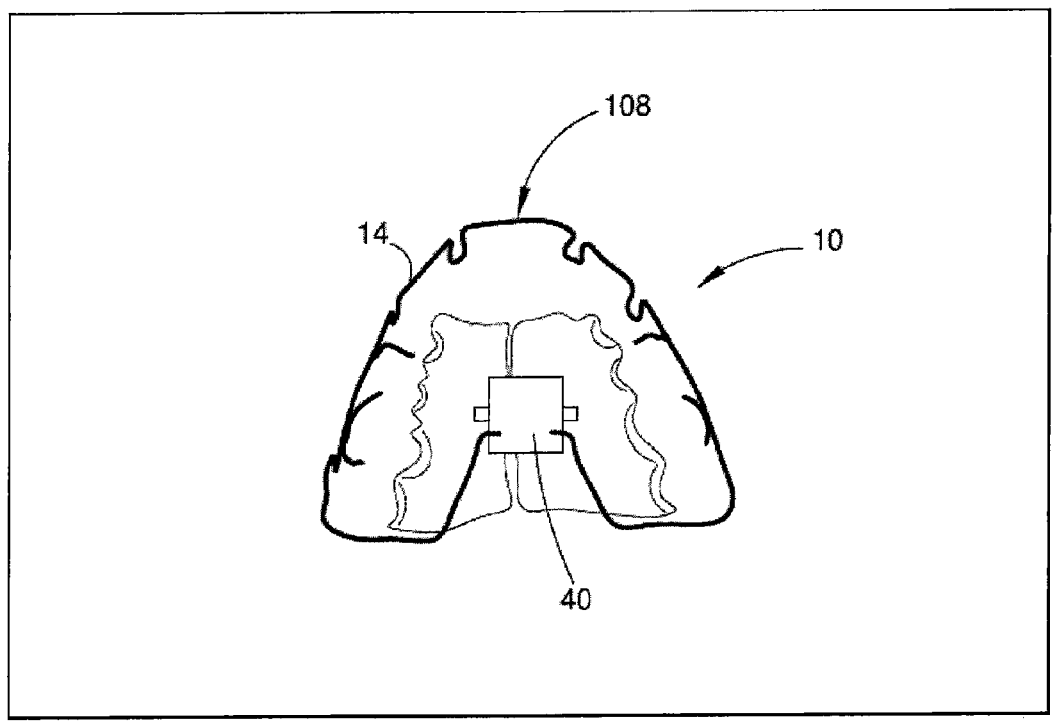
FIG. 13(c) is a perspective view of an underside of a dental appliance for an upper jaw, the appliance having an arch wire with a labial bow portion but no anterior bite plane.

FIG. 13(c) shows a further alternative removable dental appliance 10 for an upper jaw which, similar to the device shown in FIG. 13(b), has no anterior bite plane, however it does have a front labial bow portion 108 to the arch wire 14. This arrangement provides the advantage of being able to pull the upper front teeth inward by virtue of the labial bow portion 108, while allowing the patient greater freedom to talk by omission of the anterior bite plane. As with the appliance of FIG. 13(b), the appliance of FIG. 13(c) has a 2-way expansion screw mechanism 40.

Figure 14:
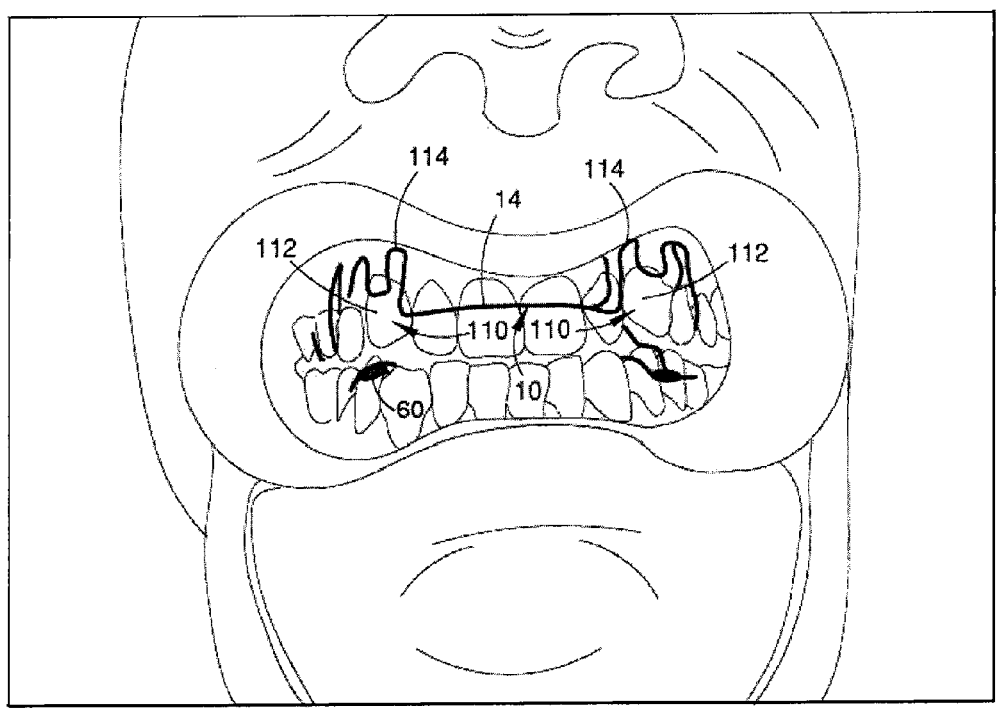
FIG. 14 is a front view of a dental appliance for an upper jaw and a dental appliance for a lower jaw, shown in place on a wearer's jaws.

FIG. 14 shows dental appliances 10, 60 for upper and lower jaws fitted in situ on the upper and lower jaws of a patient. Each of the patient's upper canines 110 have been provided with composite buttons 112 which are able to abut against portions 114 of the arch wire 14 to prevent the arch wire 14 from dropping relative to the patient's teeth, or to move the canines 110 into position.

Figure 15:
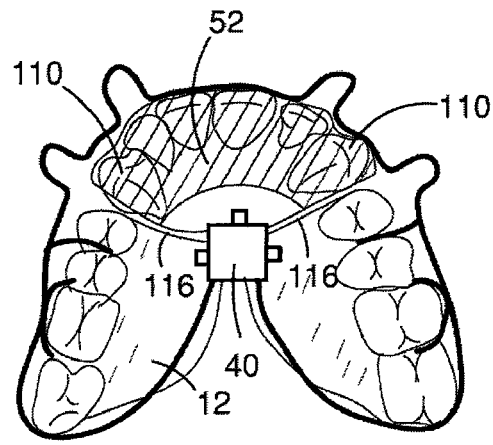
FIG. 15 is a diagrammatic view of an underside of a dental appliance shown fitted to an upper jaw.

FIG. 15 shows a diagram representing a dental appliance 10 fitted to an upper jaw of a patient. A base 12 of the appliance 10 is split to enable 3-way movement effected by way of a 3-way expansion screw mechanism 40. In general, the sectioning of the base 12 depends on which teeth are to be moved. For example, in the appliance depicted in this Figure, the front splits 116 of the sectioning are positioned so that the front panel 52 includes the upper canines 110, as opposed to the appliance 10 of FIG. 11 wherein the base 12 is sectioned such that the front panel 52 excludes the canines 110.

Figure 16:
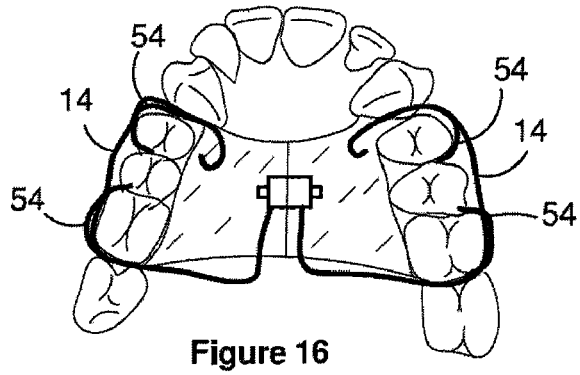
FIG. 16 is a diagrammatic view of an underside of a dental appliance shown fitted to an upper jaw, the appliance having no anterior bite plane.
Figure 17:
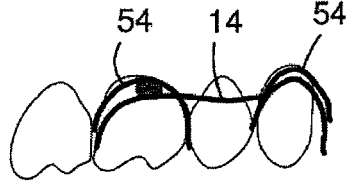
FIG. 17 is a diagrammatic side view of two C-clasps and a portion of an arch wire of a dental appliance.

FIG. 16 shows an alternative removable dental appliance 10 which, like the appliance shown in FIG. 13(b), is without an anterior bite plane or a labial bow to the arch wire 14. The base 12 of the appliance has a 2-way split, adjustable by way of 2-way expansion screw mechanism 40. FIG. 17 shows a side view of the appliance of FIG. 16 wherein C-clasps 54 are shown as being soldered at central portions thereof to the arch wire 14.

Figure 18:
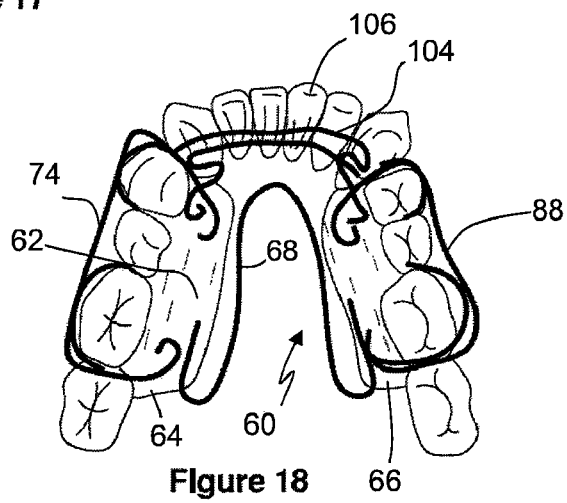
FIG. 18 is a diagrammatic top view of a dental appliance shown fitted to a lower jaw.

With reference to FIG. 18, there is shown a dental appliance similar to that shown in FIGS. 8 to 10 for a lower jaw of a wearer. The dental appliance 60 has a base 62 which is formed of a first lingual portion 64, a second lingual portion 66 and a resilient member 68 holding apart the lingual portions 64, 66. The dental appliance 60 has a first arch wire 74 and a second arch wire 88 configured in a similar manner to the corresponding features described with reference to FIGS. 8 to 10. Anterior wires or springs 104 are provided for urging forward anterior teeth 106 of the wearer.

Figure 19:
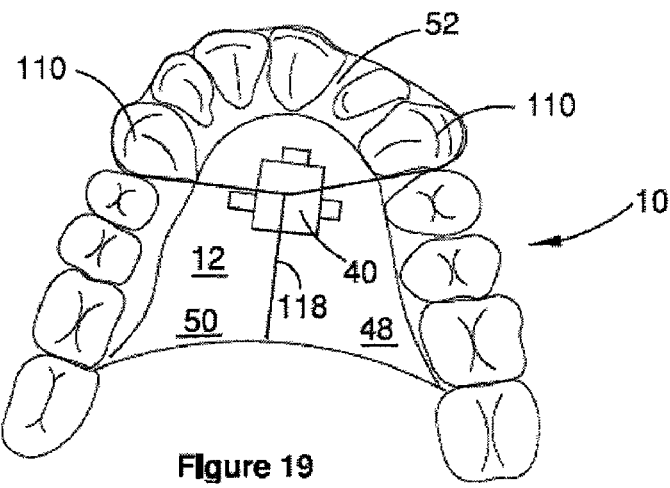
FIG. 19 is a diagrammatic view of an underside of a dental appliance shown fitted to an upper jaw.

FIG. 19 shows a removable dental appliance 10 in place on an upper jaw. The appliance has a 3-way expansion screw mechanism 40 and is sectioned so that a front panel 52 of the base 12 includes the canines 110. However, in contrast to the appliance 10 of FIG. 15, the sectioning of the base 12 is different such that, when the base 12 is contracted together by tightening the screws of mechanism 40, the side panels 48, 50 of the base 12 are brought into abutment along line 118.

Figure 20:
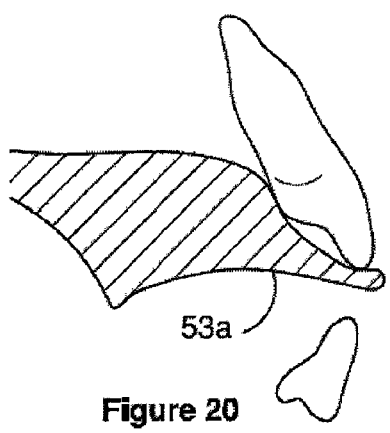
FIG. 20 is a diagrammatic cross-sectional side view of a dental appliance for an upper jaw, the appliance having a curved bite plane.
Figure 21:
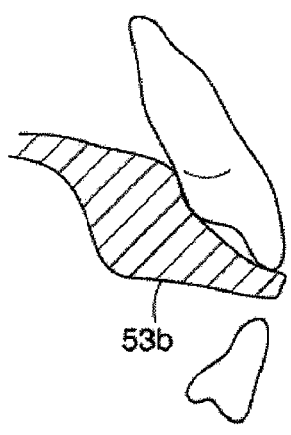
FIG. 21 is a diagrammatic cross-sectional side view of a dental appliance for an upper jaw, the appliance having a flat bite plane.
Figure 22:
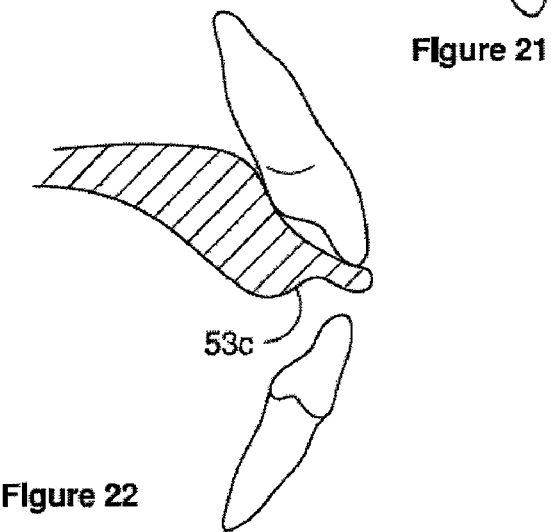
FIG. 22 is a diagrammatic cross-sectional side view of a dental appliance for an upper jaw, the appliance having a bite plane shaped for locking forward a lower jaw relative to an upper jaw.

FIGS. 20 to 22 show different configurations of bite planes 53 of removable dental appliances for upper jaws. The bite planes 53a, 53b and 53c are anterior bite planes, and are depicted by way of vertical cross sections taken along a central axis of a front portion of the dental appliance. More particularly, FIG. 20 shows a curved bite plane 53a for moving the lower jaw forwards, FIG. 21 shows a flat bite plane 53b, and FIG. 22 shows an indented bite plane 53c for positively locating the lower jaw relative to the upper jaw. The bite plane plays a big part in allowing the jaw to track forwards, allowing instant loosening of the throat muscles and soft tissues at the base of the tongue and around the larynx, creating better breathing and muscle relaxation. The bite plane may extend underneath the patient's upper front teeth, and may also optionally extend underneath the canines depending on the needs of the particular case.

Figure 23:
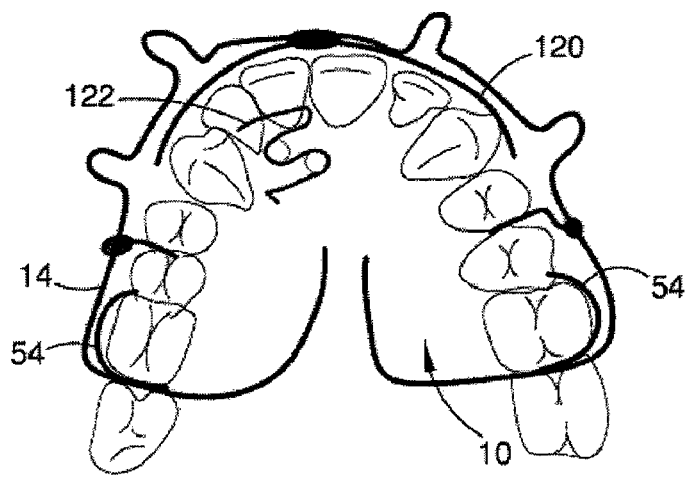
FIG. 23 is a diagrammatic view of an underside of a dental appliance shown fitted to an upper jaw, the appliance having a Z-spring.
Figure 27:
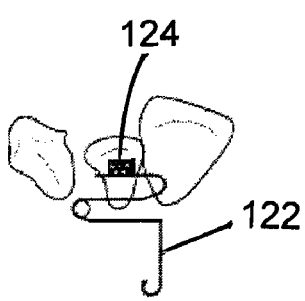
FIG. 27 is a diagrammatic front view of three teeth showing operation of a Z-spring on one of the teeth.

FIG. 23 shows a removable dental appliance 10 fitted to an upper jaw, the appliance 10 being provided with a first spring 120 for bring the canines 110 into occlusion, and a second spring in the form of a Z-spring 122 for rectifying crossbite. Dental appliances for either the upper or lower jaw may be provided with springs for tailoring movement of the wearer's teeth. The springs may be attached by soldering to the arch wire, or by embedding in the acrylic base. Z springs can engage a little composite filling material bonded to a tooth just above the spring (as shown in FIG. 27) to prevent the appliance from being unstable and coming out of the mouth. Springs etc. can be added to the arch wire by using metal bonding and resin without soldering. The dental appliance 10 shown in FIG. 23 also includes a pair of "long" C-clasps 54, each of which is soldered to the arch wire 14 at only one end portion of the C-clasp 54.

Figure 24:
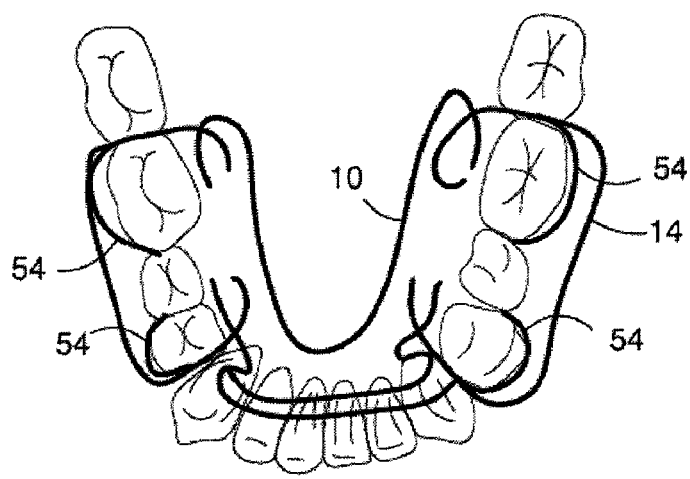
FIG. 24 is a diagrammatic top view of a dental appliance shown fitted to a lower jaw.
Figure 25:
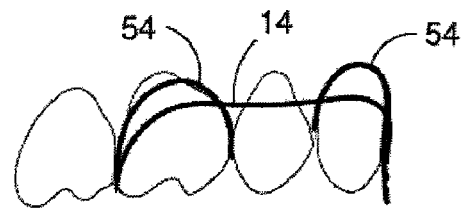
FIG. 25 is a diagrammatic right side view of a portion of the dental appliance of FIG. 24, showing two C-clasps and a portion of an arch wire of the appliance.

FIG. 24 shows a removable dental appliance 10 for a lower jaw having four "long" C-clasps 54, each of which is soldered to the arch wire 14 at only one end portion of the C-clasp 54 to provide a greater length to a cantilever portion of the clasp 54. FIG. 25 shows a right side view of the dental appliance 10 of FIG. 24, and clearly depicts the manner in which the C-clasps 54 are soldered to the arch wire 14. As discussed earlier, by virtue of the longer cantilever portion suspended form the arch wire 14, the "long" C-clasps provide improved retention when compared to a C-clasp attached at a centre portion thereof to the arch wire. The cantilever portion is able to flex relative to the arch wire 14 to a greater degree, thus allowing improved sutural movement.

Figure 26:
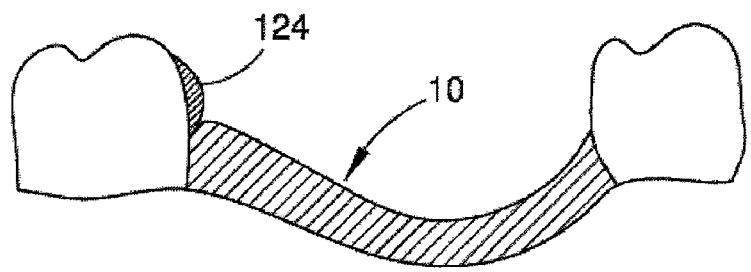
FIG. 26 is a diagrammatic lateral cross-sectional view of a dental appliance shown fitted to a wearer's jaw.
Figure 28:
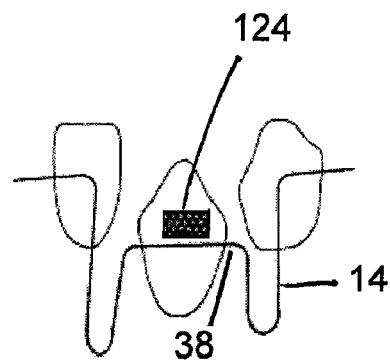
FIG. 28 is a diagrammatic front view of three teeth showing operation of U-loops in an arch wire of a dental appliance.
Figure 29:
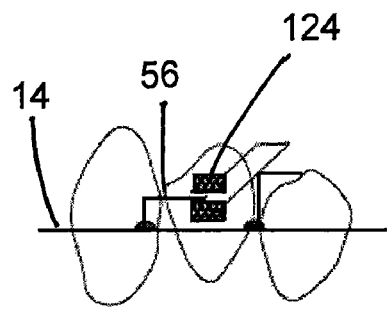
FIG. 29 is a diagrammatic front view of three teeth showing operation of L-rests fitted to an arch wire of a dental appliance.

FIG. 26 shows a lateral cross-section of a dental appliance 10 when fitted to an upper jaw of a patient. Composite filling material can be added onto teeth as indicated by reference numeral 124 to give greater undercut for retention purposes. This is particularly useful in the case where there are difficulties in retaining a dental appliance to baby teeth. Composite can also be applied to teeth (as shown in FIGS. 28 and 29) to help position the arch wire and also move teeth, like eye teeth either labially or lingually.

Dental appliances in accordance with examples of the present invention facilitate easy installation to a wearer's jaw or jaws, and are more comfortable compared to conventional previously proposed dental appliances, affording the teeth greater freedom to move. Further, as the arches are able to be widened by use of the present appliance, the need for extractions is reduced. The arrangement of clasp and arch wire can be used in a greater variety of situations when compared to previously proposed appliances, and even in cases previously of low retention. Retention may be improved by widening the base by adjusting the expansion screw and by trimming the acrylic so that pressure is applied to teeth that need to be moved outward. The pressure should be gentle and slow, and the widening allows the teeth to be realigned with greater freedom. Such realignment can be directed by the arch wire and by auxiliary wires or springs either soldered to the arch wire or fixed into the acrylic. Slight lateral expansion of premolars and molars if done correctly allows the pressure on cranial sutures to free up allowing jaw restriction to ease to varying extents, thus having a beneficial effect on the nervous system. The bigger the mouth opens the more the entire body relaxes.

Due to the way the acrylic is on the inside and the arch wire is on the outside, teeth can move in 6 directions to achieve harmony. That is forwards and backwards, side to side and up and down.

Use of appliances in accordance with examples of the invention can promote realignment of the wearer's jaws, particularly by encouraging forward movement of the lower jaw, as well as improved ability of the patient to close his/her mouth and to breathe through the nose.

Manufacture of the Appliance

In order to manufacture a dental appliance as described above for a patient, impressions of the patient's jaws are taken, and models of the jaws are made from these impressions. It is desirable for the impressions and models to have a high degree of accuracy such that the appliance can be manufactured to fit well and to work effectively.

The detail should go right back to, and include, the rearmost teeth. Lower impressions require as much of the lingual plate as possible. When impressions are taken using alginate, they must be poured before they dry out. Models can be poured up next day if kept wet. Rubber impressions also can be good. They give the option of several pours, including study models. A new type of alginate, cum rubber, may be a problem solver; it is lighter for posting to laboratories and also less work for the staff. When taking impressions, after selecting a suitable tray for supporting the impression material, the loaded impression should be first pressed in backwards. This will avoid gagging the patient, and also prevent forcing the material to the back of the throat. Staff should ensure a good mixture, which is not too runny.

Instructions to the Laboratory a) There are two basic designs of appliance and some variations. Usually the laboratory is asked for a standard upper jaw or lower jaw appliance which is the basic design. The standard upper jaw appliance has two main variations; with or without labial bow. The one without is for patients who need to speak or, for aesthetics, do not want any wire to show in the front. Whenever there is a TMJ problem, the upper jaw appliance should be a TMJ standard 3-way type which is expandable in 3 ways so as to allow greater control. If there is going to be no bite plane and the palate is free at the front, then a 2-way type appliance can be used.

b) The outside labial bow is standard in design but can be modified and additions can be made, such as adding little finger springs to move the canines into place or putting selective pressure on any teeth. The retention is by way of C-clasps soldered or lasered to wire to engage the teeth. There is also frictional retention from the arch wire which can be tightened or loosened by adjusting the U-loops. It may be necessary to place composite buttons on teeth labially or lingually to provide adequate retention. When the retention is good, patient compliance is better. If there is a problem, it is better to take impressions again and refit or remake rather than antagonise the outcome. The good news is that even if the patient does not wear this appliance for a long time, it can be refitted quite easily—unlike when using Adams type devices in which the constant strain causes wire fatigue and breakage.

c) Class III cases are slightly different and mostly require only an upper appliance with posterior occlusal planes. A 3-way expansion is required to create as much maxillary growth as possible. Sometimes it is worthwhile to add composite to lower molars to open up the bite and allow the centrals and laterals to move forward and encourage an edge-to-edge bite at least.

Basic Records to Take Before Commencing Treatment

1. An Ortho Pantomo Gram (OPG) to look for any abnormalities, like teeth missing or abnormally positioned, or fractures etc.

2. A Cephalogram which can be useful in difficult cases and as a standard record.

3. Study models—this is the starting point to see future changes from here.

4. Ensure care is taken and hygiene control is carried out.

5. A thorough nutrition history.

6. A good visual inspection of the tonsils and breathing. Ascertain tonsil size (walnut, plum, olive or pea). Gag reflex indicates inflammation of the throat, or sensitivity.

7. It may be beneficial to advise the patient to avoid dairy, gluten, grains such as wheat, rye etc, and sugar. Also, thyroid over-stimulating foods such as chocolate, coffee should be avoided.

8. The range of jaw movements and measurements, and deviations. A measurement of the jaw opening is a must. It is one of the best indicators of muscle relaxation. The bigger the mouth opening, the easier the breathing and head posture with less body pain, especially headaches.

9. Photographic records are very useful to map the progressive change in structure of the face and full body picture to indicate the posture.

10. Blood tests may be necessary with some patients to see endocrine problems.

11. A full health questionnaire is useful in older patients.

12. In TMJ cases, a full Tufts questionnaire can be done to note such conditions as earache; neck stiffness; TMJ pain; TMJ joint click; headaches; facial pain; arm pain/tingling/numbness; neck pain/stiffness; upper back pain/stiffness; lower body pain/stiffness, and range of motion of the jaw.

13. Geometric analysis of the models in order to line up the lower jaw and upper jaw in correct symmetrical position without being influenced by muscle contraction.

Appliance Adjustment Tips

Retention can be increased by adding composite to the lingual or buccal surface to create an undercut or button for Z springs on the anterior teeth. Composite may be applied to canines to lift or draw them into place. Wires can be soldered or glued on with acrylic.

Springs should be lightly adjusted frequently, even weekly, and then the results are very rapid. A button of composite prevents springs from lifting and also helps in the retention of the appliance.

Contra-Indications

Never create pain or too much pressure. Braces may be used in addition to use of the appliance to achieve a fine finished product if perfection is what is desired. However, in many cases braces are not necessary. The position of unerupted canines should be determined prior to proclining a lateral incisor, so as not to damage the roots. A good knowledge of TMJ and occlusal balancing may be necessary for more difficult cases. TMJ cases are very easily corrected with this method. Creating space for teeth before moving them out is also advised. Orthodontic changes may require the appliances to be worn day and night, whereas some cases can be resolved just by night-time use.

The above dental appliances have been described by way of example only and modifications are possible within the scope of the invention. Other features, may also be added onto the arch wire or base as required to move teeth as necessary. Lip bumpers may also be added.

Dental appliances according to examples of the present invention may be used in the following applications:

In the treatment of simple and some complex orthodontic cases, especially for young children before the use of braces. In some cases braces can be totally avoided.

In the treatment of TMJ with relief of headaches and tension, allowing greater improvement in jaw opening.

In the treatment of clenching and squeezing the face to allow changes in the shape of the face, and in some cases changing patterns of mouth breathing by widening the maxilla as early as is possible.

As a splint to give relief in clenching patterns.

For tightening up the upper lip and loosening the chin and neck muscles.

For the treatment of sleep apnoea and bed wetting or difficult sleeping.

In the treatment of asthma for improved breathing.

As an active or passive TMJ appliance to alter muscle forces, to alter growth and guide dental development, muscle function and correct bad habits.

As a general retainer to refine and maintain and even complete orthodontic treatment after the braces are removed.

To help to correct asymmetrical jaws to some degree and angulation of the smile line (cant), due to uneven muscle contraction of the face.

In helping to shrink tonsils and adenoids, and improve breathing.

In the treatment of migraines, headaches, neck problems, RSI, backaches and leg pain, tinnitus and snoring.

This system can also be used for people that have missed out on braces or find braces too expensive, which gives another alternative to fix malocclusion and TMJ problems in a simple easy manner.

The reference to any prior art in this specification is not, and should not be taken as, an acknowledgment or any form of suggestion that that prior art forms part of the common general knowledge in Australia.

The invention claimed is:

1. A removable dental appliance having a base adapted for locating inside of an arch of teeth of a wearer and an arch wire coupled to the base, an outer surface of the base being contoured for contact with inner surfaces of the teeth, arranged such that when in use the arch wire extends around an outer periphery of a set of the wearer's teeth with no interconnection between the arch wire and the base existing intermediate the set of teeth, and the dental appliance is provided with an expansion screw for expanding the base, wherein the arch wire extends from one side posterior portion of the base to the other side posterior portion of the base for contact with outer surfaces of the set of teeth along an outside of the arch of teeth, and the arch wire exits the posterior portions on each side of the base at locations spaced from the arch of teeth, the arch wire extending from the posterior portions indirectly, generally rearwardly and outwardly relative to the wearer when in situ, to the set of teeth in bent portions of wire on each side of the base so as to allow flexure of the bent portions of wire between the base and the set of teeth, thereby promoting limited movement of the arch wire relative to the base when the dental appliance is in use.

2. A dental appliance as claimed in claim 1, wherein the dental appliance is provided with a 3-way expansion screw mechanism for enlarging the maxilla of the wearer in left, right and anterior directions relative to the wearer.

3. A dental appliance as claimed in claim 1, wherein the dental appliance is for an upper jaw of the wearer.

4. A dental appliance as claimed in claim 1, wherein, when the dental appliance is in use, the arch wire extends continuously from a left side posterior portion of the base, outwardly behind a posterior tooth on the left side of the arch, forwardly along the outside left side of the arch, rightward along the outside front side of the arch, rearwardly along the outside right side of the arch, and inwardly behind a posterior tooth on the right side of the arch to a right side posterior portion of the base, relative to the wearer.

5. A dental appliance as claimed in claim 1, wherein the arch wire incorporates four U-loops.

6. A dental appliance as claimed in claim 1, wherein the arch wire is provided with one or more C-clasps.

7. A dental appliance as claimed in claim 6, wherein at least one of the C-clasps is coupled to the arch wire at only one end portion of the C-clasp.

8. A dental appliance as claimed in claim 1, wherein the base is provided with a bite plane.

9. A dental appliance as claimed in claim 8, wherein the bite plane is an anterior bite plane.

10. A dental appliance as claimed in claim 8, wherein the bite plane is a posterior bite plane.

11. A dental appliance as claimed in claim 1, wherein at each side posterior portion the arch wire extends within the base to the expansion screw so as to form a closed circuit.

* * * * *

UNITED STATES PATENT AND TRADEMARK OFFICE
CERTIFICATE OF CORRECTION

PATENT NO. : 7,661,955 B2  Page 1 of 1
APPLICATION NO. : 10/573986
DATED : February 16, 2010
INVENTOR(S) : Joseph Da Cruz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 305 days.

Signed and Sealed this

Thirtieth Day of November, 2010

David J. Kappos
*Director of the United States Patent and Trademark Office*